United States Patent
Berman et al.

(10) Patent No.: US 8,920,364 B2
(45) Date of Patent: Dec. 30, 2014

(54) BIOMATERIAL DELIVERY DEVICE

(71) Applicant: Medtronic Xomed, Inc., Jacksonville, FL (US)

(72) Inventors: Phillip J. Berman, Jacksonville, FL (US); Matthew J. Friend, Jacksonville, FL (US); Ethan G. Sherman, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 13/781,331

(22) Filed: Feb. 28, 2013

(65) Prior Publication Data

US 2014/0243792 A1     Aug. 28, 2014

(51) Int. Cl.
*A61M 13/00*     (2006.01)
*A61M 31/00*     (2006.01)
*A61J 7/00*     (2006.01)

(52) U.S. Cl.
CPC .. *A61M 31/00* (2013.01); *A61J 7/00* (2013.01)
USPC ............................................ 604/58; 604/514

(58) Field of Classification Search
USPC ........... 604/57–64, 500–522, 309, 27, 36, 38, 604/187, 218, 221, 225, 228
See application file for complete search history.

(56) References Cited

U.S. PATENT DOCUMENTS

| | | | |
|---|---|---|---|
| 39,889 A | 9/1863 | Crossman | |
| 1,642,950 A | 9/1927 | Haas | |
| 1,678,562 A | 7/1928 | Edens | |
| 1,684,999 A | 9/1928 | Levy, Jr. | |
| 2,151,418 A | 3/1939 | Bolte | |
| 2,664,891 A | 1/1954 | Kempel | |
| 2,672,144 A | 3/1954 | Cohen | |

(Continued)

FOREIGN PATENT DOCUMENTS

| | | |
|---|---|---|
| CN | 201643226 | 11/2010 |
| EP | 0 405 320 A2 | 1/1991 |

(Continued)

OTHER PUBLICATIONS

"Eppendorf Combitips® Eppendorf Combitips® Plus" Product Information Sheets, Eppendorf North America, Inc., 8 pages (2005).

(Continued)

*Primary Examiner* — Bhisma Mehta
*Assistant Examiner* — Tien Tran
(74) *Attorney, Agent, or Firm* — IPLM Group, P.A.

(57) ABSTRACT

A biomaterial delivery device includes an elongated handheld powder storage conduit with proximal and distal ends and a bore having a central axis. The proximal end is closed by a movable powder dispensing actuator, and the distal end is closed by an openable sealing nib moveable from its closed to its open position by force upon the actuator. The distal end has a distally-projecting powder discharge chute that spaces the nib away from a surgical site. When the device is held upright over a surgical site with the nib opened, powder passing the nib is deflected at a first oblique direction with respect to the central axis and into or onto the powder discharge chute, and powder striking the chute is deflected at a rotationally distinct second oblique direction orientation with respect to the central axis and into or onto the surgical site.

27 Claims, 4 Drawing Sheets

(56) References Cited

U.S. PATENT DOCUMENTS

| | | |
|---|---|---|
| 2,754,590 A | 7/1956 | Cohen |
| 3,816,921 A | 6/1974 | Malmin |
| 4,015,753 A | 4/1977 | Bennett |
| 4,261,488 A | 4/1981 | Bennett |
| 4,307,823 A | 12/1981 | Heiss et al. |
| 4,356,941 A | 11/1982 | McRoskey et al. |
| D270,183 S | 8/1983 | Govenius |
| 4,468,218 A | 8/1984 | Armstrong |
| 4,492,576 A | 1/1985 | Dragan |
| 4,515,586 A | 5/1985 | Mendenhall et al. |
| 4,769,011 A | 9/1988 | Swaniger |
| 4,776,704 A | 10/1988 | Kopunek et al. |
| 4,801,008 A | 1/1989 | Rich |
| 4,801,263 A | 1/1989 | Clark |
| 4,963,093 A | 10/1990 | Dragan |
| 4,973,246 A | 11/1990 | Black et al. |
| 5,033,463 A | 7/1991 | Cocozza |
| D331,970 S | 12/1992 | Creamer, Jr. |
| 5,181,918 A | 1/1993 | Braudhorst et al. |
| 5,244,388 A | 9/1993 | Frush |
| 5,259,537 A | 11/1993 | Beers et al. |
| 5,286,257 A | 2/1994 | Fischer |
| 5,322,440 A | 6/1994 | Steele |
| 5,429,122 A | 7/1995 | Zanen et al. |
| 5,490,615 A | 2/1996 | Robbins et al. |
| D368,963 S | 4/1996 | Gomes |
| 5,513,630 A | 5/1996 | Century |
| 5,520,174 A | 5/1996 | Evans et al. |
| 5,549,564 A * | 8/1996 | Yoon .................... 604/164.12 |
| 5,554,136 A | 9/1996 | Luther |
| D374,932 S | 10/1996 | Engelman |
| 5,591,408 A | 1/1997 | Belgardt et al. |
| 5,620,660 A | 4/1997 | Belgardt et al. |
| 5,620,661 A | 4/1997 | Schürbrock |
| 5,624,406 A | 4/1997 | Labouze |
| 5,642,730 A | 7/1997 | Baran |
| D384,162 S | 9/1997 | Husar et al. |
| D384,163 S | 9/1997 | Husar et al. |
| 5,676,130 A | 10/1997 | Gupte et al. |
| D387,426 S | 12/1997 | Husar et al. |
| 5,694,920 A | 12/1997 | Abrams et al. |
| 5,758,967 A | 6/1998 | King |
| 5,800,059 A | 9/1998 | Cooke et al. |
| 5,816,804 A | 10/1998 | Fischer |
| 5,816,805 A | 10/1998 | Cheetham |
| 5,829,434 A | 11/1998 | Ambrosio et al. |
| 6,013,050 A | 1/2000 | Bellhouse et al. |
| 6,027,471 A * | 2/2000 | Fallon et al. .................... 604/59 |
| 6,059,570 A | 5/2000 | Dragan et al. |
| 6,099,307 A | 8/2000 | Discko, Jr. |
| 6,210,377 B1 | 4/2001 | Ouchi |
| 6,238,212 B1 | 5/2001 | Khachatoorian et al. |
| 6,267,269 B1 | 7/2001 | Kates |
| 6,283,946 B1 * | 9/2001 | Fischer .................... 604/218 |
| RE37,760 E | 6/2002 | Mathison et al. |
| 6,408,846 B1 | 6/2002 | Ohki et al. |
| 6,416,322 B2 | 7/2002 | Qualliotine et al. |
| 6,540,072 B1 | 4/2003 | Fischer |
| 6,550,957 B2 | 4/2003 | Mizutani et al. |
| 6,585,511 B2 | 7/2003 | Dragan et al. |
| 6,682,348 B2 | 1/2004 | Lawter et al. |
| 6,808,091 B2 | 10/2004 | Njaastad |
| 6,814,072 B1 | 11/2004 | Seppälä |
| 6,878,338 B2 | 4/2005 | Taylor et al. |
| 6,886,560 B1 | 5/2005 | Seppälä |
| 6,926,003 B2 | 8/2005 | Seppälä |
| 6,976,842 B1 | 12/2005 | Miggantz |
| 6,990,974 B2 | 1/2006 | Staniforth et al. |
| 7,040,893 B2 | 5/2006 | Fischer |
| 7,089,934 B2 | 8/2006 | Staniforth et al. |
| 7,179,085 B2 | 2/2007 | Dorsey et al. |
| 7,185,648 B1 | 3/2007 | Rand |
| 7,207,967 B1 | 4/2007 | Bellhouse et al. |
| D554,264 S | 10/2007 | Watson et al. |
| 7,357,789 B2 | 4/2008 | Bills |
| 7,431,587 B2 | 10/2008 | Pond |
| 7,547,292 B2 | 6/2009 | Sheldrake et al. |
| D603,113 S | 10/2009 | Morton |
| 7,740,479 B2 | 6/2010 | Allred |
| 7,834,065 B2 | 11/2010 | Nakajima et al. |
| 7,922,043 B2 | 4/2011 | Luechinger |
| 8,037,880 B2 | 10/2011 | Zhu et al. |
| 8,066,510 B2 | 11/2011 | Ho et al. |
| D655,812 S | 3/2012 | Ramini |
| 8,127,763 B2 | 3/2012 | Smyth et al. |
| 8,132,565 B2 | 3/2012 | Von Schuckmann |
| 8,210,171 B2 | 7/2012 | Denny et al. |
| 8,226,599 B2 | 7/2012 | Engle |
| D685,087 S | 6/2013 | Voic |
| D685,466 S | 7/2013 | Moshinsky |
| 8,622,997 B2 | 1/2014 | Shippert |
| 2002/0017295 A1 | 2/2002 | Weers et al. |
| 2002/0119417 A1 | 8/2002 | Ashman |
| 2002/0177562 A1 | 11/2002 | Weickert et al. |
| 2005/0005933 A1 | 1/2005 | Seppälä et al. |
| 2005/0155901 A1 | 7/2005 | Krueger et al. |
| 2006/0100572 A1 | 5/2006 | DiMatteo et al. |
| 2007/0151562 A1 | 7/2007 | Jones et al. |
| 2007/0264310 A1 | 11/2007 | Hissong et al. |
| 2007/0272763 A1 | 11/2007 | Dunne et al. |
| 2008/0168987 A1 | 7/2008 | Denny et al. |
| 2008/0185000 A1 | 8/2008 | Schuckmann |
| 2008/0223365 A1 | 9/2008 | Von Schuckmann |
| 2008/0281289 A1 | 11/2008 | Lewis |
| 2009/0013994 A1 | 1/2009 | Jones et al. |
| 2009/0025721 A1 | 1/2009 | Ellwanger et al. |
| 2009/0142728 A1 * | 6/2009 | Lawter et al. .................... 433/89 |
| 2009/0227943 A1 * | 9/2009 | Schultz .................... 604/77 |
| 2009/0260626 A1 | 10/2009 | Von Schuckmann |
| 2009/0291911 A1 | 11/2009 | Myntti et al. |
| 2010/0300441 A1 | 12/2010 | Von Schuckmann et al. |
| 2011/0036870 A1 | 2/2011 | Lüchinger |
| 2011/0178495 A1 * | 7/2011 | Ji .................... 604/500 |
| 2011/0220242 A1 | 9/2011 | Yang et al. |
| 2011/0251580 A1 | 10/2011 | Greenhalgh et al. |
| 2012/0103332 A1 | 5/2012 | Parsons |
| 2012/0108509 A1 | 5/2012 | Hissong et al. |
| 2012/0111326 A1 | 5/2012 | Mayer et al. |
| 2013/0000639 A1 | 1/2013 | Galluppi et al. |

FOREIGN PATENT DOCUMENTS

| | | |
|---|---|---|
| EP | 1 093 767 B1 | 3/2005 |
| FR | 2 787 717 | 6/2000 |
| GB | 628675 | 9/1949 |
| GB | 761588 | 11/1956 |
| GB | 1127201 | 9/1968 |
| GB | 357180 | 9/1981 |
| JP | 10 263421 A | 10/1998 |
| JP | 2009-131629 A | 6/2009 |
| WO | WO 2004/043533 A2 | 5/2004 |
| WO | WO 2008/125402 A1 | 10/2008 |
| WO | WO 2008138007 A1 | 11/2008 |
| WO | WO 2009/132229 A2 | 10/2009 |
| WO | WO 2011/059953 A1 | 5/2011 |
| WO | WO 2011/149436 A1 | 12/2011 |

OTHER PUBLICATIONS

Arista® Absorbable Hemostatic Particles AH Product Information Sheets, Medafor Hemostatic Polymer Technologies, 3 pages downloaded from http://www.medafor.com/products/arista.aspx on May 2, 2012.

DryPette® Hand Held Manual Powder Dispensing System, Product Information Sheets, Zinsser Analytic, 4 pages (2009).

* cited by examiner

BIOMATERIAL DELIVERY DEVICE

FIELD OF THE INVENTION

This invention relates to devices for delivering hygroscopic powdered biomaterials to surgical sites located in or near the respiratory tract.

BACKGROUND

Adenoids (pharyngeal tonsils) and tonsils (palatine tonsils) are involved in a number of diseases of the ear, nose, and throat including chronic otitis media with effusion (COME), recurrent acute otitis media (RAOM), adenoiditis, pediatric chronic sinusitis, tonsillitis, pediatric obstructive sleep apnea (OSA), adult OSA, and chronic strep throat. Lingual tonsils can become infected and may cause or aggravate sore throat pain. Initial treatment for these various conditions normally involves administration of oral medications or, in the case of pediatric and adult sleep apnea, use of a continuous positive airway pressure (CPAP) device. Otitis media may be treated using ventilation tube surgery. Treatment success rates are often less than optimal, and in many cases the tonsils, adenoids or other throat tissue eventually may be surgically removed. Such surgeries are however painful, typically require the administration of anesthetics and lengthy post-operative recovery periods, and may be accompanied by complications such as post-operative bleeding, dehydration, weight loss, peritonsillar abscess, torticilis (neck stiffness), tissue regrowth, repeat surgery to address incomplete prior tissue removal, continued COME or RAOM, continued OSA, and occasionally death. Existing post-surgical treatments generally provide only limited relief, and may include dietary limitations, rinses, and administration of painkilling medications or oral antibiotics to reduce post-operative pain and infections.

U.S. Patent Application Publication No. US 2012/0108509 A1 (the disclosure of which is incorporated herein by reference) describes an artificial scab composition for use in tonsillectomy, adenoidectomy and uvulopalatopharyngoplasty (UPPP) procedures. The composition is a substantially dry, free-flowing powdered mixture of at least partially solvatable chitosan particles and at least partially solvatable oxidized polysaccharide particles. When applied to a surgical site or wound moistened with bodily fluids, the powdered mixture forms an inhomogeneous, uncohesive, solid sheet-like body that breaks apart into smaller pieces if peeled away from the surgical site or wound. The powdered mixture may for example be applied using a bellows-type dispenser that expels the powder through an elongated, flexible straw that directs a stream of the powder onto a surgical site.

SUMMARY OF THE INVENTION

If not aimed carefully or if excessive force is applied to the bellows, the above-described dispenser can inadvertently direct some or all of the powdered mixture into a human patient airway rather than on to the intended surgical site. Doing so is undesirable for a variety of reasons including potential patient safety risk and added delay in completing a surgical procedure.

Once the powder has been dispensed, it usually is desirable to spread the powder over the surgical site, e.g., over the floor, walls and pillars of each tonsillar fascia, so as to form a thin film of the applied biomaterial. Doing so typically may require removal of the dispensing device from the patient's mouth and insertion of a spreading instrument, as there may not be sufficient room or viewing space to leave both the dispenser and spreading instrument in place while using one or the other. If upon spreading it appears that insufficient powder was applied, it may be necessary to remove the spreading instrument, reinsert the dispenser to apply more powder, and then to remove the dispenser and reinsert the spreading instrument to complete the procedure. Moreover, because it may be desirable to carry out spreading promptly after dispensing, a surgeon may prefer to complete all dispensing and spreading of powder on a first tonsillar fascia before dispensing and spreading powder on the remaining fascia. This too may necessitate repeated removal and insertion of the dispenser and spreading instrument.

It may also be desirable to retract nearby tissue while applying or spreading the powder. This may require insertion of an additional instrument into an already crowded operating field.

From the foregoing, it will be appreciated that what is needed in the art is a powdered biomaterial delivery device that can dispense and spread biomaterial powders in tonsillectomy, adenoidectomy, UPPP and other surgical procedures near patient airways. Such devices and methods for their use are disclosed and claimed herein.

The invention provides in one aspect a biomaterial delivery device comprising an elongated handheld powder storage conduit sized for use in the mouth of a human patient and containing finely-divided powdered sterile biomaterial, the conduit having a proximal end, a distal end, and a bore having a central axis, the proximal end being closed by a movable powder dispensing actuator, the distal end (a) being closed by an openable sealing nib that can be moved from its closed to its open position by force upon the actuator and (b) having a distally-projecting powder discharge chute that spaces the nib away from a surgical site, wherein when the device is held over a surgical site with the proximal end uppermost and the nib actuated to its open position, powder passing the nib is deflected by the device at a first oblique direction with respect to the central axis and into or onto the powder discharge chute, and powder striking the chute is deflected by the device at a rotationally distinct second oblique direction with respect to the central axis and into or onto the surgical site.

The invention provides in another aspect a method for applying a powdered biomaterial to a surgical site near a supine human patient airway, the method comprising the steps of:

a) holding in a generally upright position an elongated handheld powder storage conduit containing finely-divided powdered sterile biomaterial, the conduit having a proximal end, a distal end, and a bore having a central axis, the proximal end being closed by a movable powder dispensing actuator, the distal end (i) being closed by an openable sealing nib that can be moved from its closed to its open position by force upon the actuator and (ii) having a distally-projecting powder discharge chute that spaces the nib away from a surgical site, wherein when the device is held over a surgical site with the proximal end uppermost and the nib actuated to its open position, powder passing the nib is deflected by the device at a first oblique direction with respect to the central axis and into or onto the powder discharge chute, and powder striking the chute is deflected by the device at a rotationally distinct second oblique direction with respect to the central axis and into or onto the surgical site, and b) applying force to the actuator so that powder is dispensed in non-atomized form past the nib and towards the surgical site.

Figures 1, 2:
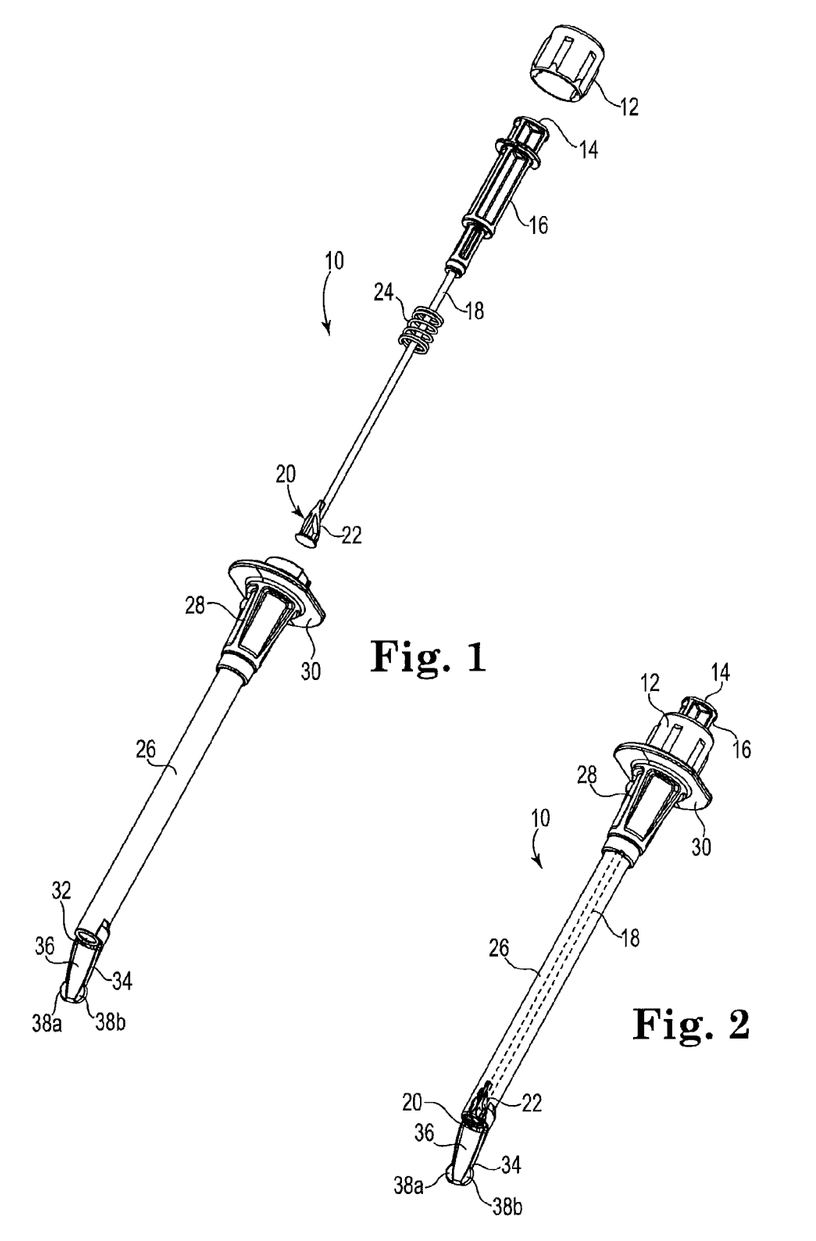

The disclosed device and method enable rapid and accurate administration of powdered biomaterials onto or into surgical site near an airway of a supine patient. The disclosed nib desirably serves as a dump valve and powder deflector. The disclosed chute desirably serves as a further powder deflector that directs the falling powder onto a desired small target area. The chute desirably is formed in an inclined face of an angled tip having additional surfaces or contours that are usable for distributing or spreading the powder in or on a surgical site, and for retracting nearby tissue as need be. The disclosed device and method desirably permit single instrument gravitationally-assisted powder dispensing, distribution and spreading without requiring the application of pressure on a cross-section of the powder itself (e.g., from a piston, plunger, compressed gas or other propellant) to force powder out of the device. This facilitates rapid and readily controllable operation by surgical personnel, and helps discourage aerosolization or inadvertent misdirection of biomaterial powder into the patient airway rather than into or onto the intended surgical site.

BRIEF DESCRIPTION OF THE DRAWING

FIG. 1 is an exploded view of one embodiment of the disclosed biomaterial dispensing device;

FIG. 2 is a perspective view, partially in phantom, of the assembled FIG. 1 device;

FIG. 3 is a side orthogonal view of the assembled FIG. 1 device, sectioned along line A-A' in FIG. 4;

FIG. 4 is a distal end view and

FIG. 5 is a side view of the assembled FIG. 1 device;

FIG. 6 is a perspective view of the FIG. 1 nib;

FIG. 7 is a perspective view of the distal end portion of the assembled FIG. 1 device showing the nib in its closed position;

FIG. 8 is a perspective view of the distal end portion of the assembled FIG. 1 device showing the nib in its open position; and FIG. 9 through FIG. 15 show various views of the disclosed tips.

Like reference symbols in the various figures of the drawing indicate like elements.

DETAILED DESCRIPTION

The following detailed description describes certain embodiments and is not to be taken in a limiting sense. The terms shown below have the following meanings:

The term "airway" means a mammalian breathing passage, e.g., as formed by the mouth, nose, throat and trachea.

The term "average inside diameter" when used in reference to a filled powdered delivery device having (a) a distal powder delivery outlet and (b) a powder-containing conduit having a central axis, a cylindrical or other cross-section and a constant or varying cross-sectional area along that axis means the diameter of a right circular cylinder having a height and volume like the height and volume circumscribed by the powder when the central axis of the filled device is aligned vertically with the outlet closed and directed downward.

The term "biomaterial" when used in reference to a substance means that the substance may be introduced into (and if need be left in) the body of a patient as part of a surgical procedure without significant deleterious or untoward effects upon the body.

The term "free-flowing" when used in reference to a powdered material means the powder will spontaneously flow downhill when placed on a horizontal surface and the surface rotated to an inclination of about 45° to 60° from the horizontal.

The term "gravitational assistance" when used in reference to a powdered substance dispensed from an outlet means that the substance passes through the outlet primarily due to the influence of gravitational forces, and The term "hygroscopic" when used in reference to a powdered substance means that the substance takes up and retains water while in solid form (for example, by adsorption, absorption, or as chemically-bound water of hydration).

The term "loosely-filled" when used in reference to a powdered substance in a conduit or other container means that the substance is not packed into the container and will rearrange itself within the container if the container is slowly inverted without shaking.

The term "non-atomized" when used in reference to a powdered substance dispensed from an outlet means that a gaseous propellant is not used to accelerate the substance through the outlet or past the outlet (e.g., via the Bernoulli effect).

FIG. 1 is a perspective exploded view depicting components that may be used in an embodiment 10 of the disclosed biomaterial delivery device. FIG. 2 depicts a perspective view partly in phantom, of the assembled FIG. 1 device. Retainer 12 is located at the proximal end of device 10 and provides a sleeve with openings sized to fit over and capture the end 14 of powder dispensing actuator 16. In the embodiment shown in FIG. 1 and FIG. 2, actuator 16 is integrally molded with an elongated and cylindrical, rod-like or stem-like member 18 that can be moved distally along the central axis of device 10 by depressing actuator 16 toward the distal end of device 10. Actuator 16 is integrally molded with an elongated and cylindrical, rod-like or stem-like member 18 that can be moved distally along the device 10 central axis. Spring 24 biases actuator 16 toward the proximal end of device 10. Nib 20 at the distal end of elongated member 18 serves as a dump valve for a finely-divided powdered sterile biomaterial powder (not shown in FIG. 1) that will be contained in and dispensed by device 10. Nib 20 includes a powder-deflecting ramp 22 that alters the trajectory of powder particles falling past ramp 22 by directing the particles at a first oblique direction with respect to the device 10 central axis. In the embodiment shown in FIG. 1 and FIG. 2 (and as may be seen more clearly in FIG. 6), ramp 22 is concave (e.g., scoop-like) with respect to an axis perpendicular to the main powder flow direction so as to encourage the powder to remain in contact with ramp 22 as the powder is redirected and to discourage the powder from merely rebounding off ramp 22. The disclosed ramp may instead have a generally flat face or may have other non-flat configurations, for example, concave (e.g., trough-like) with respect to the main powder flow direction so as to direct the falling particles into a laterally more concentrated or narrower pattern as or after they leave ramp 22 or convex (e.g., domed) with respect to the main powder flow direction so as to direct the falling particles into a laterally broadened pattern as or after they leave ramp 22.

Member 18 fits loosely inside the bore of generally cylindrical or barrel-shaped conduit 26 so that powder may freely flow between member 18 and the inner sidewalls of conduit 26. In the embodiment shown in FIG. 1, conduit 26 has a central cylindrical bore having a uniform inside diameter (and accordingly the same value for its average inside diameter) and a central axis, common with the central axis of elongated member 18, along which the movable components of device 10 may reciprocally move towards and away from the distal end of device 10. In the embodiment shown in FIG. 1 and FIG.

2, the device central axis and the conduit or bore central axis are the same, and unless the context clearly indicates otherwise these terms may be used interchangeably. Actuator 16 desirably is sized to fit snugly but slidably inside a complementary cylindrical opening in grip 28. Flange 30 on grip 28 assists a user of device 10 in holding, moving and actuating device 10 in one gloved hand, for example by holding device 10 with grip 28 placed between, and the distal surface of flange 30 in contact with, the user's gloved thumb and second finger or gloved first and second fingers, while meanwhile depressing actuator 16 using the free gloved index finger or free gloved thumb of the same hand. Meanwhile the user desirably may also tilt, rotate, press against, withdraw from or otherwise move device 10 as need be with respect to the surgical site.

The distal outlet end 32 of device 10 is connected to a distally-projecting and preferably angled tip 34. One face of tip 34 houses a distally-projecting powder-receiving and powder-delivering discharge chute 36 whose chute sidewalls (as may be better seen in FIG. 14) open toward the central axis of device 10. Tip 34 spaces nib 20 away from a surgical site or other moist tissue surface, thereby helping to minimize moisture entry into device outlet 32 and discourage clogging. Chute 36 receives falling powder particles deflected by ramp 22, and guides or otherwise deflects the received powder particles in a rotationally distinct second oblique direction (e.g., with a rotational orientation with respect to the device 10 central axis that is 180° different than the above-mentioned first oblique direction). The thus-deflected powder particles are guided or otherwise directed by chute 36 into or onto a desired surgical site. In the embodiment shown in FIG. 1, the sidewalls of chute 36 converge as they approach the distal end of chute 36, thereby helping to focus or concentrate the falling particles as or after they pass the distal end of chute 36.

In the embodiment shown in FIG. 1, tip 34 also includes gently-rounded and flattened wing portions 38a and 38b which project laterally in hammerhead fashion away from the distal end of chute 36. Wing portions 38a and 38b help in spreading and packing down the applied biomaterial, as well as widening and thereby reducing the pressure per unit area applied by the backside of tip 34 when tip 34 is pressed against a surgical site. Wing portions 38a and 38b and (as may be better seen in FIG. 5) the gently-rounded backside of tip 34 are especially well adapted for manipulating (for example, retracting) tissue and for raking and spreading the dispensed powder across the floor and up and down the sidewalls of a surgical site, e.g., a tonsillar fascia. The oblique angled orientation of tip 34 (viz., the acute angle of tip 34 with respect to the device 10 central axis) further assists a user in retracting tissue, raking dispensed powder backwards across a tonsillar fascia floor, raking dispensed powder up the sidewalls of and into pockets or pillars in tonsillar fascia, and lining up the device outlet above the region at which dispensed powder is desired to land. The respective oblique angles of chute 36 and the ramp 22 with respect to the device 10 central axis may each or both be chosen to help regulate the dispensed powder flow rate, with more oblique angles or more abrupt changes in direction generally causing reduced flow rates, and less oblique angles or less abrupt changes in direction generally causing increased flow rates. The gently-rounded contours and the absence of sharp edges on nib 20 and especially on tip 34 also help minimize surgical site trauma while device 10 is being used to dispense, distribute or spread powder.

Tip 34 may be firmly connected to the device, for example by being integrally molded with conduit 26. If desired, tip 34 may instead be removable by a user and replaceable or interchangeable with other tips having different sizes (e.g., pediatric and adult sizes) or different shapes or anatomically specific features that better adapt the tip to the intended surgical site, for example by providing specialized working surfaces that assist in depositing or spreading the biomaterial in complex or unusual surgical sites.

In the embodiment shown in FIG. 1 and FIG. 2, elongated member 18 and the interior of conduit 26 each have a constant diameter. The tendency of some powders (for example, hygroscopic powders) to form clumps or cause clogging inside device 10 can be ameliorated by providing a plurality of powder-contacting clump-disrupting projections arrayed inside and along the length of the conduit between the actuator and the nib, the projections being movable in the direction of the device 10 central axis by force upon the actuator. Further details regarding such projections or regarding the presently-disclosed device may be found in copending U.S. patent application Ser. Nos. (13/781,072, 29/447,060 and 29/447,079), filed even date herewith and the disclosures of which are incorporated herein by reference.

Figures 3, 4:
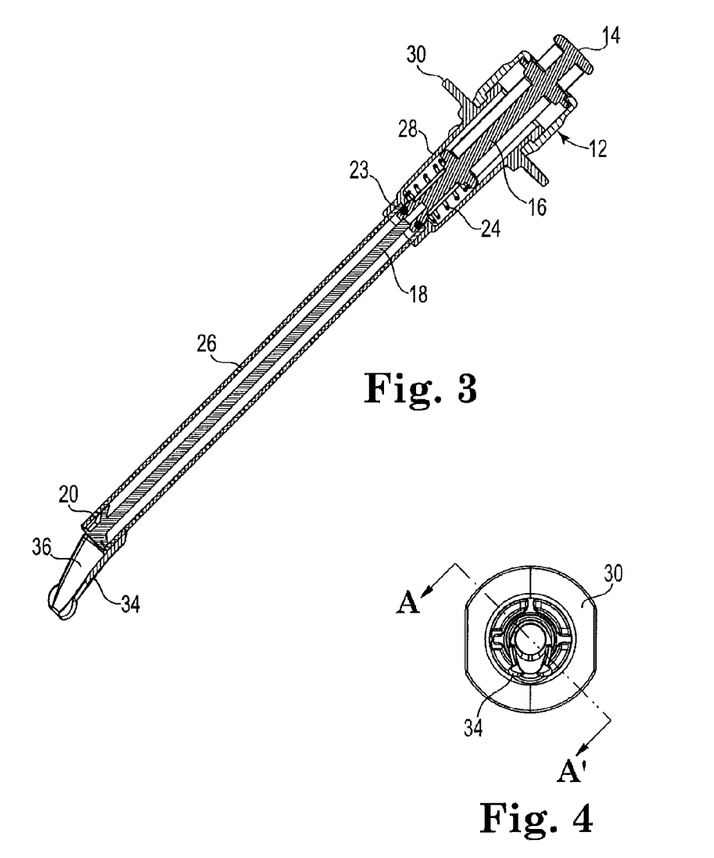

FIG. 3 depicts is a side orthogonal view of the assembled FIG. 1 device, sectioned along line A-A' in FIG. 4. The components shown in FIG. 3 are like those in FIG. 1 and FIG. 2 but with the addition of a sealing O-ring 23.

Figure 5:
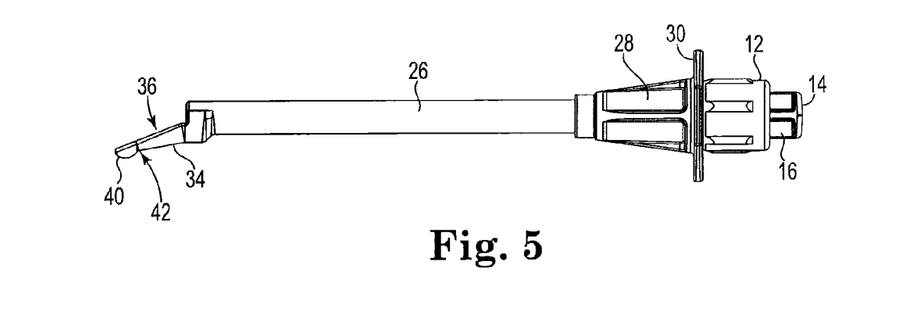

FIG. 4 depicts a distal end view and FIG. 5 depicts a side view of the assembled FIG. 1 device. Gently rounded dome 40 on the backside of tip 34 faces away from chute 36. Dome 40 can serve among other things to distribute and thereby reduce the pressure per unit area applied by the edge of tip 34 when tip 34 is pressed against a surgical site. Dome 40 is especially well adapted for manipulating (for example, retracting) tissue and for raking and spreading the dispensed powder across the floor and up and down the sidewalls of a surgical site, e.g., a tonsillar fascia. The small concave seam (see arrow 42) where the proximal perimeter of dome 40 meets the backside of tip 34 provides an especially desirable improvement in powder raking and tissue retraction performance.

Figures 6, 7, 8:
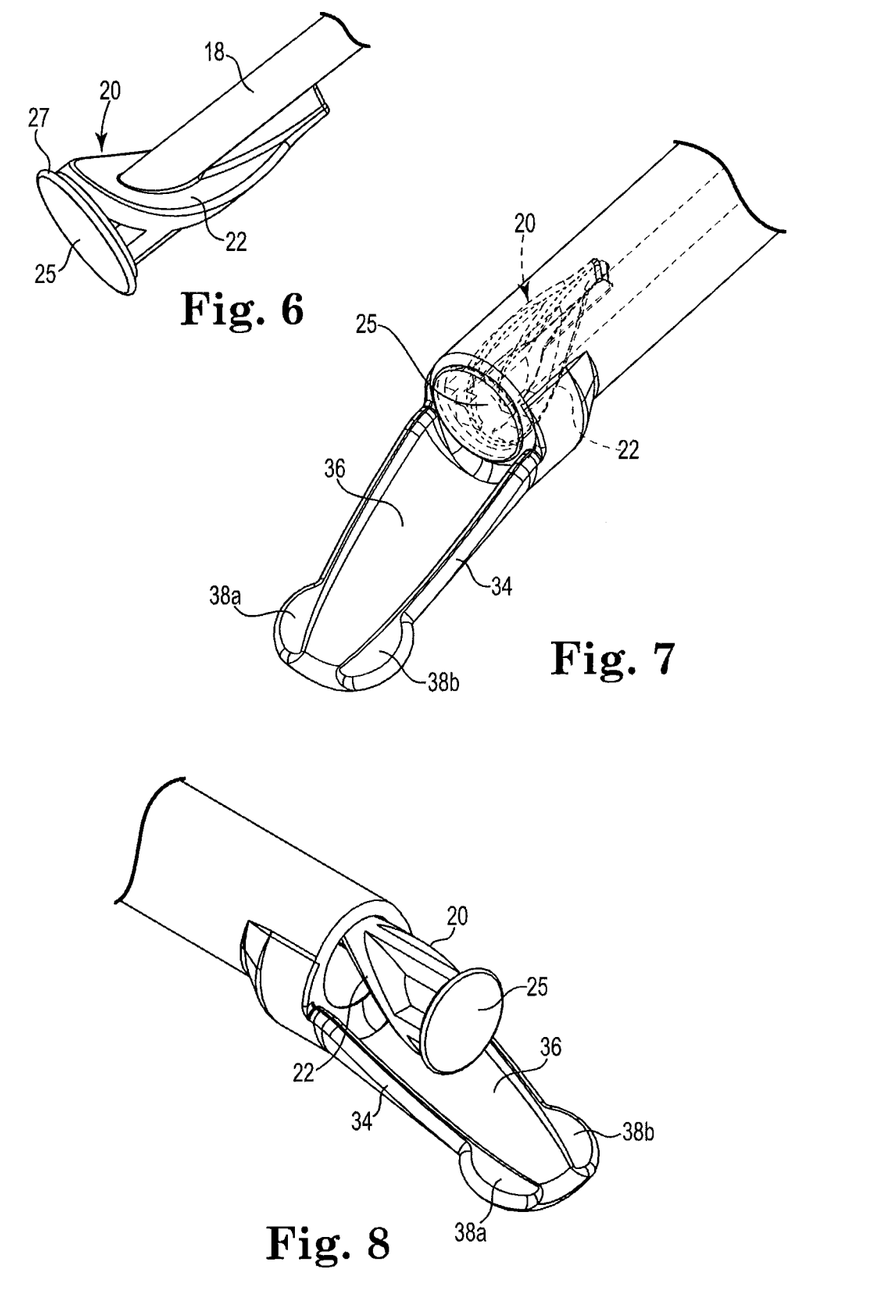
Figure 9:
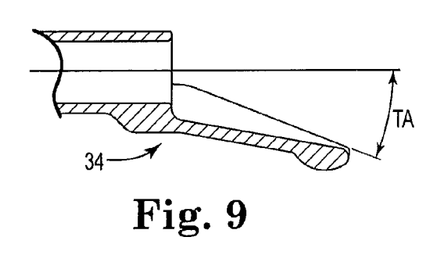

FIG. 6 depicts a perspective view of nib 20. Ramp 22 directs substantially all the falling powder away from the device 10 central axis. Ramp 22 does so by deflecting the falling powder at a first angled orientation with respect to the central axis and into or onto powder discharge chute 36 of tip 34 (not shown in FIG. 6). The end portion 25 of nib 20 also includes a discharge outlet sealing surface 27 that discourages powder from passing out of (and discourages powder, liquids and other materials from entering) the conduit when nib 20 is in its closed position.

FIG. 7 and FIG. 8 respectively depict perspective distal end portion views of the assembled FIG. 1 device showing nib 20 in its closed (FIG. 7) and open (FIG. 8) positions. FIG. 8 provides an especially useful illustration of the changes in powder direction that can arise when powder is deflected from ramp 22 to chute 36 while nib 20 is in the open position.

FIG. 9 through FIG. 15 provide several views of tips for use in the disclosed device. Most of the individual lead lines and numeric identifiers having been omitted for clarity. FIG. 9 depicts a cross-sectional view of tip 34 through the device 10 central axis. The Angle TA may be referred to as the Tip Angle and may for example be about 4 to about 60, about 4 to about 50, about 6 to about 40 or about 8 to about 20 degrees with respect to the central axis. Steeper angles may make it easier to retract tissue, but may also make it more difficult to direct the dispensed powder onto a desired part of a surgical site.

FIG. 10 depicts a side view of tip 34. The length TL may be referred to as the Tip Length and may for example be about 10 to about 30, about 14 to about 25 or about 16 to about 20 mm measured from the device outlet to the distal end of tip 34. TL values above about 12 mm are desirable in order to keep the nib dry during use, and values of about 12 to about 18-20 mm are desirable for use on pediatric and adult tonsillar fascia.

Figure 10:
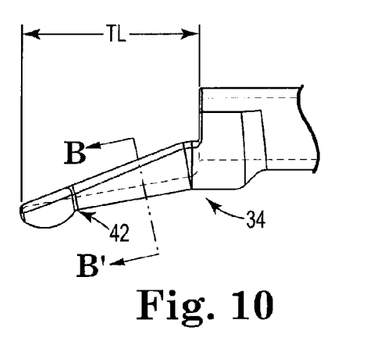
Figure 11:
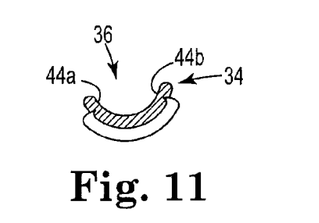

FIG. 11 depicts a sectional view of tip 34, sectioned along line B-B' in FIG. 10. Sidewalls 44a and 44b in trough 36 help guide the falling powder direct it toward the intended surgical site.

Figure 12:
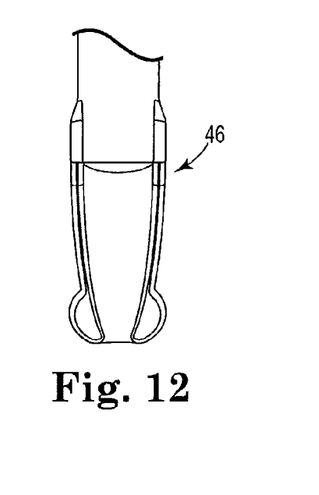

FIG. 12 depicts the backside of tip 46. Tip 46 is like tip 34 but lacks dome 40. Tip 46 tends to have less effective spreading, raking and tissue retracting performance than a tip having the disclosed backside dome.

Figure 13:
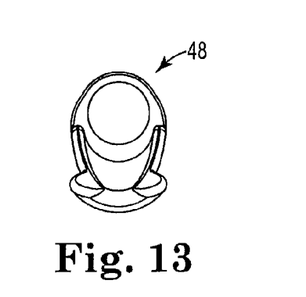
Figure 14:
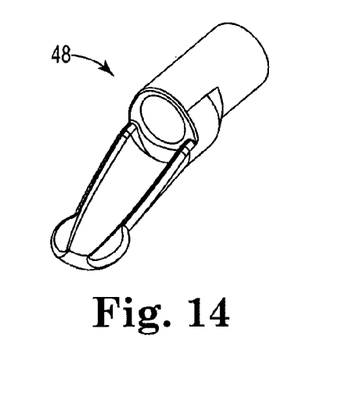
Figure 15:
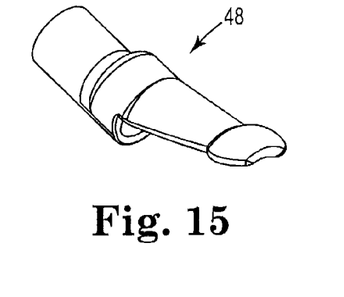

FIG. 13, FIG. 14 and FIG. 15 are three views of a removable and replaceable tip 48. FIG. 13 shows a view from the distal end toward the proximal end of tip 48. FIG. 14 and FIG. 15 are respectively three quarter perspective views of the trough side (FIG. 14) and backside (FIG. 15) of tip 48.

The disclosed biomaterial delivery device may be made in a variety of other embodiments. A number of design goals may be borne in mind when doing so. For example, the device is as mentioned sized for use in the mouth of a human patient, and desirably is sized for use above surgical sites located in the back of the throat of a supine human patient of adolescent or adult age. In general for such use there will be a desirable balance between the thinness of the device and the rapidity with which it can be used to dispense a needed quantity of biomaterial powder. Desirably the device when inserted through an open patient mouth and directed towards the tonsillar fascia is sufficiently thin so as to leave ample viewing room and space to insert and if need be to operate or manipulate other instruments or objects such as suction lines, lights, retractors (e.g., Hurd retractors) or fingers, e.g., for a hand other than the hand used to operate the disclosed device. The device desirably also is sufficiently long so that the dispenser when so inserted and directed will reach the back of the patient's throat. The device desirably has sufficiently great powder capacity and sufficiently rapid powder delivery capability to enable the desired powder amount to be dispensed, distributed and spread as need be in minimal time, e.g., in less than two minutes, less than one minute or less than 30 seconds per tonsillar fascia for a tonsillectomy procedure. The device desirably provides a line of site view enabling a user to see simultaneously the chute, previously dispensed powder and the area on which powder will be dispensed with the next device actuation. The device desirably is shaped to enable handheld, one-hand operation using either hand. The device may however be made in a variety of diameters and lengths, and may for example have a conduit with an outer diameter of about 4 to about 15 mm, an average inside diameter of about 5 to about 13 mm, and a length measured from the finger grip to the device outlet of about 10 to about 20 cm for use on tonsillar fascia and longer lengths (for example about 10 to about 25 cm) for use in nasal and sinus procedures. The disclosed flange desirably has a diameter of about 20 to about 40 mm, and may be equipped with flattened circumferential portions to keep the device from rolling when placed on a tray, table or other horizontal surface.

Desirably the device can be rotated at least 360° around its central axis while in the mouth, e.g., in order to switch from right-handed to left-handed use, or to facilitate reorientation of the device such as when changing from one tonsillar fascia to the other. Accordingly, the device desirably does not include airlines or other potentially interfering appendages.

The device desirably can be used by itself to both dispense and spread metered amounts of powder and form a continuous powder coating over the entire surgical site. The device desirably is straight along the entire length of the conduit, as that can provide better visibility during use, and can provide better leverage and control when spreading powder using the tip.

The device desirably meters out an incremental powder portion each time the actuator is operated. The metered amount will be a function of several factors including the actuator stroke length and geometry, the chosen design for the elongated member and projections (if used), the chosen design for any seals employed, the device outlet size and shape, and the chosen nib design, tip design and associated angles. The device desirably permits dispensing to occur whether or not the device distal end is in contact with tissue or other surface, and desirably may be operated from its proximal end to dispense powder while the distal end is inserted in a patient's mouth without touching the back of the throat. The device also desirably permits dispensing to occur without having to shake the device. The device desirably is non-pressurized ("non-air-assisted"), does not aerosolize the dispensed powder, and delivers most or all of the dispensed powder to the intended surgical site and none or substantially none of the dispensed powder to the surrounding tissue or the patient airway. The device accordingly would not be regarded as an inhaler. The delivered biomaterial desirably falls down the conduit and through the device outlet primarily or exclusively due to gravitational forces, and desirably is not forced out of the device due to the action of a piston or other component that applies force to the entire cross-sectional area of the dispensed powder portion. The device preferably does not dispense powder or at least a significant quantity of powder if the device outlet is opened while the device is horizontal. The device desirably keeps its powder dry until such time as the dispensed biomaterial contacts the surgical site. Desirably at least the portion of the device housing the stored biomaterial (e.g., the conduit) and optionally also the elongated member, projections (if used) and tip are transparent or translucent. The use of transparent or translucent components can assist a surgeon in metering a desired powder amount during a procedure and at least initially in seeing where best to spread the powder.

The disclosed actuator preferably has a reciprocating actuation motion and more preferably a reciprocating motion along the device central axis. The motion desirably is in the distal direction, although an upward actuation in the proximal direction could be employed by using a suitable ledge or grip to facilitate lifting the actuator. The actuator may if desired use a rotating actuation motion but desirably does do so as such actuation may be more difficult to carry out while holding the device in a single gloved hand. For actuation using a reciprocating motion along the device central axis, actuation desirably requires a relatively short (e.g., about 2 to about 12, about 4 to about 12 or about 6 to about 10 mm) stroke and a moderate but noticeable (e.g., about 1 to about 4 Kg) force. Desirably the actuator (or if desired, one or more other components such as a projection or projections or the nib) are provided with one or more small ribbed or grooved portions that engage a nearby complementary recess or tang so as to provide a click stop or other tactile feedback actuation feature. The recited tactile feedback may for example occur during or at the end of an actuation stroke. The tactile feedback may also provide accompanying vibrations that can help agitate the powder. The disclosed actuator, elongated member, projections (if used) and nib desirably are connected to one another so that actuation causes all to move (e.g., reciprocate) together. The actuator desirably is provided as part of a component integrally molded with at least the nib.

The disclosed nib desirably serves as both a closure valve for the device outlet and as a deflector that directs falling powder away from the device central axis and into a complementary chute structure in the disclosed tip. The nib may for example be connected to the actuator via the disclosed elongated member or may be opened and closed using some other connecting structure. Preferably the nib, elongated member and projections (if used) are formed (e.g., molded) as a single integral component. The nib preferably discourages the powdered biomaterial from falling into areas where it is not intended to be placed and preferably also provides tactile feedback of dispenser actuation.

The disclosed conduit preferably has a bore (and most preferably a circular bore) whose diameter does not diminish along the length of the device from its proximal to distal ends. Reductions in bore diameter near the proximal end may not be a matter of concern, but reductions in bore diameter near the distal end and especially near the device outlet desirably are avoided. The device outlet preferably has the same cross-sectional shape as the bore (e.g., is circular for a circular bore), preferably is as large as possible, and preferably has a diameter at least 75%, at least 80%, at least 90% or at least as large as the conduit average inside diameter.

The disclosed chute desirably directs the majority and preferably all of the falling powder onto a desired small target area that is displaced laterally from the device central axis. The chute diameter, measured as a chord between the tops of the chute sidewalls, desirably is about 5 to about 13 mm proximate the nib and about 3 to about 9 mm proximate the distal end of the chute. The tip desirably has a maximum width at its distal end that is at least about 120%, at least about 150%, at least about 200% or at least 300% as wide as the chute diameter at the chute distal end. The above-mentioned Tip Angle desirably is less than 90° with respect to the device central axis. The direction at which dispensed powder exits the device desirably does not change with successive operations (e.g., strokes) of the device actuator. The tip desirably lacks sharp edges that might cause tissue trauma, and desirably includes wings or other powder spreading appendages with rounded distal edges. The tip desirably is sufficiently stiff to permit spreading and tamping the dispensed powder without noticeable tip deflection. The tip may however be bendable or otherwise formable to accommodate particular anatomical features or surgical sites.

The disclosed device and its non-powdered components may be made from a variety of materials including acrylics, olefins such as polyethylene and polypropylene, polycarbonates and other suitable thermoplastic or thermoset materials. The chosen materials desirably have a low tendency to adhere to the chosen biomaterial powder whether due to static or other attractive forces. The device may also include antistatic surface treatments, antistatic additives or surface finishes chosen so as to further discourage powder adhesion.

A wide variety of powdered biomaterials may be packaged in the disclosed device. The biomaterials preferably are organic but for some surgical end uses may be inorganic materials (e.g., calcium carbonates, zeolites and other minerals or salts). Exemplary biomaterials may for example be natural materials (e.g., polysaccharides), chemically modified natural materials (e.g, polysaccharide reaction products including oxidized, acetylated, deacetylated, acid-reacted, anhydride-reacted, esterified, neutralized, base-reacted, vinyl-group reacted, isocyanate-reacted or otherwise functionalized polysaccharides, polysaccharide salts and other polysaccharide derivatives), or synthetic materials (e.g., polyglycolides, polyactides, poly(lactide-co-glycolides), poly(ϵ-caprolactones), poly(dioxanones), polyanhydrides, polyorthoesters, polyethylene glycols and polyvinyl alcohols). The powder may be a single material or mixture of materials (for example, a mixture of a crosslinkable material and a crosslinker). Exemplary biomaterials include agars, alginates, carrageenans, celluloses, chitins, chitosan, chondroitin sulfates, dextrans, galactomannans, glycogens, hyaluronic acids, starches, oxidized cellulose, oxidized chitin, oxidized chitosan, oxidized chondroitin sulfate, oxidized dextran, oxidized glycogen, oxidized hyaluronic acid, oxidized starch and other materials that will be known to persons having ordinary skill in the art. Suitable biomaterials may be obtained from a variety of commercial sources including CarboMer Inc., Monomer-Polymer and Dajac Labs, Inc. and Sigma-Aldrich Co. The powdered biomaterial desirably is obtained in dry particulate form, for example, as free-flowing granules whose average particle diameter is less than about 1 mm, less than about 100 μm, about 1 to about 80 μm, or less than 1 μm. The powdered biomaterial may be comminuted, lyophilized, crystallized or recrystallized if desired. If a mixture of particles is employed, the particles desirably are intimately mixed together prior to placement in the device, and further mixing desirably is not required at the point of use. The biomaterial may provide a variety of features such as the formation of a protective, mucoadhesive, biodegradable, bioresorbable, drug eluting or hemostatic structure (e.g., a layer) following application to a surgical site. The biomaterial preferably is substantially collagen-free and more preferably contains no collagen at all so as to be saleable worldwide for use without restriction in humans. The biomaterial may optionally include a variety of other ingredients that are themselves dry, or which when mixed with the biomaterial will provide or can be processed (e.g., dried) to provide a dry powdered biomaterial. Exemplary such other ingredients include acids, antifoam agents, antimicrobial agents, antioxidants, antistatic agents, bases, buffering agents, colorants, flow aids, hyperosmolar agents, indicators, flavoring agents, sweetening agents, therapeutic agents, modifiers to alter the release rate of therapeutic agents, and other adjuvants that will be familiar to persons having ordinary skill in the art. For example, a useful list of therapeutic agents may be found in U.S. Patent Application Publication No. US 2007/0264310 A1. The biomaterials desirably do not contain ingredients which might potentially harm mucosal tissues or structures. The disclosed device is especially desirable for dispensing hygroscopic powders that are prone to clumping or sticking. The disclosed device desirably contains the total volume of material to be used in an intended surgical procedure, for example about 0.5 to 2 grams per device for tonsillectomy procedures.

The disclosed devices desirably are ready-to use items designed for one-time use. Following filling with the desired biomaterial powder, the device typically will be placed in suitable sealed packaging (for example, a metalized foil pouch and optional box) and subjected to sterilization prior to shipment to an end user. Exemplary sterilization techniques will be familiar to persons having ordinary skill in the art, and include gamma radiation, electron beam (E-Beam) processing, and cold ionizing radiation sterilization (e.g., cold E-Beam sterilization) as described in published PCT Application No. WO 2009/132229 A2.

The disclosed device typically will be used by a surgeon near the conclusion of a surgical procedure. For example, a tonsillectomy or adenoidectomy may be carried out using traditional steps, with tissue excavation being performed using electrocauterization, snares, scalpels or other techniques, followed promptly thereafter by use of the device to dispense and desirably also to distribute or spread a coating of the disclosed powdered biomaterial on the exposed fascia. The application technique is not unlike frosting a cake using the backside of a spoon, but may be carried out much more quickly. Some surgeons may prefer to apply several metered powder doses and then spread the powder, and others may prefer repeatedly to apply a powder dose, spread the powder and repeat until a desired degree of coating is obtained. As a general guide, a desirable application rate may be about 10-25 actuations per tonsil dispensing about 0.02 to 0.05 g per actuation stroke.

Although specific and in some cases preferred embodiments have been illustrated and described, it will be appreciated by those of ordinary skill in the art that a wide variety of alternate or equivalent embodiments calculated to achieve the same purposes may be substituted for the specific embodiments shown and described without departing from the present invention. This application is intended to cover any adaptations or variations of the preferred embodiments discussed herein. Therefore, it is manifestly intended that this invention be limited only by the claims and the equivalents thereof.

We claim:

1. A biomaterial delivery device comprising an elongated handheld powder storage conduit sized for use in the mouth of a human patient and containing finely-divided powdered sterile biomaterial, the conduit having a proximal end, a distal end, and a bore having a central axis, the proximal end being closed by a movable powder dispensing actuator, the distal end (a) being closed by an openable sealing nib that can be moved from its closed to its open position by force upon the actuator and (b) having a distally-projecting powder discharge chute that spaces the nib away from a surgical site, wherein when the device is held over a surgical site with the proximal end uppermost and the nib actuated to its open position, powder passing the nib is deflected by the device at a first oblique direction with respect to the central axis and into or onto the powder discharge chute, and powder striking the chute is deflected by the device at a rotationally distinct second oblique direction with respect to the central axis and into or onto the surgical site.

2. The device according to claim 1 wherein the powder is free-flowing and hygroscopic.

3. The device according to claim 1 wherein the powder comprises a polysaccharide, polysaccharide reaction product or polysaccharide derivative.

4. The device according to claim 1 wherein the actuator has a reciprocating actuation motion along the central axis.

5. The device according to claim 1 wherein the actuator dispenses about 0.02 to 0.05 g powder per actuation.

6. The device according to claim 1 wherein the actuator has one or more ribbed or grooved portions that engage a complementary recess or tang so as to provide a click stop or other tactile feedback actuation feature.

7. The device according to claim 1 wherein the nib comprises a powder-deflecting ramp that directs substantially all passing powder away from the central axis.

8. The device according to claim 7 wherein the nib ramp is concave with respect to an axis perpendicular to the main powder flow direction so as to encourage passing powder to remain in contact with the ramp as the powder is deflected and discourage passing powder from rebounding off the ramp.

9. The device according to claim 1 wherein the nib comprises a discharge outlet sealing surface that discourages liquids from entering the conduit when the nib is in its closed position.

10. The device according to claim 1 wherein the actuator and nib are integrally molded.

11. The device according to claim 1 wherein the chute directs the majority of passing powder onto a target area displaced laterally from the central axis.

12. The device according to claim 1 wherein the chute has a distal end, and sidewalls that converge as they approach the chute distal end, thereby helping to concentrate the passing powder.

13. The device according to claim 12 wherein the chute has a diameter, measured as a chord between the tops of the chute sidewalls, of about 5 to about 13 mm proximate the nib and about 3 to about 9 mm proximate the chute distal end.

14. The device according to claim 1 further comprising a tip having gently-rounded and flattened wing portions which project laterally away from the distal end of the chute and assist in powder spreading.

15. The device according to claim 14 wherein the tip has a distal end with a maximum width at least about 120% of the chute diameter proximate the chute distal end.

16. The device according to claim 14 wherein the tip lacks sharp edges that might cause tissue trauma.

17. The device according to claim 14 wherein the tip has a backside domed portion that assists in retracting tissue and in raking and spreading dispensed powder across the floor and up and down the sidewalls of a surgical site.

18. The device according to claim 14 wherein the tip is sufficiently stiff to permit spreading and tamping the dispensed powder without noticeable tip deflection.

19. The device according to claim 14 wherein the tip is firmly connected to the device.

20. The device according to claim 14 wherein the tip is removable by a user from the device and replaceable or interchangeable with tips having different sizes, different shapes or anatomically specific features that better adapt the tip to a surgical site.

21. The device according to claim 14 wherein the tip extends at an angle of 4 to 60 degrees with respect to the central axis and has a length of 10 to 30 mm.

22. The device according to claim 1 wherein the device permits single instrument gravitationally-assisted powder dispensing, distribution and spreading without requiring the application of pressure on a cross-section of the powder itself to force powder out of the device, and may be operated from its proximal end to dispense powder while the distal end is inserted in a patient's mouth but does not touch the back of the patient's throat.

23. The device according to claim 1 wherein the device is non-air-assisted, does not aerosolize the dispensed powder, and can be rotated at least 360 ° around its central axis while in a patient's mouth.

24. The device according to claim 1 wherein the device can be operated with one gloved hand and provides a line of site view enabling a user to see simultaneously the chute, previously dispensed powder and the area on which powder will be dispensed with the next device actuation, and can be used by itself to retract tissue.

25. The device according to claim 1 wherein the device keeps its powder dry until such time as dispensed powder contacts a surgical site, and delivers most or all of the dispensed powder to the surgical site and none or substantially none of the dispensed powder to surrounding tissue or a patient airway.

26. The device according to claim 1 wherein the device is in sealed sterilized packaging.

27. method for applying a powdered biomaterial to a surgical site near a supine human patient airway, the method comprising the steps of:

a. holding in a generally upright position an elongated handheld powder storage conduit containing finely-divided powdered sterile biomaterial, the conduit having a proximal end, a distal end, and a bore having a central axis, the proximal end being closed by a movable powder dispensing actuator, the distal end (i) being closed by an openable sealing nib that can be moved from its closed to its open position by force upon the actuator and (ii) having a distally-projecting powder discharge chute that spaces the nib away from a surgical site, wherein when the device is held over a surgical site with the proximal end uppermost and the nib actuated to its open position, powder passing the nib is deflected by the device at a first oblique direction with respect to the central axis and into or onto the powder discharge chute, and powder striking the chute is deflected by the device at a rotationally distinct second oblique direction with respect to the central axis and into or onto the surgical site, and b. repeatedly applying force to the actuator so that powder is dispensed in non-atomized form and in a series of incremental portions past the nib and towards the surgical site.

* * * * *